United States Patent
O'Connor et al.

(10) Patent No.: US 8,809,004 B2
(45) Date of Patent: Aug. 19, 2014

(54) DETECTION OF FELINE IMMUNODEFICIENCY VIRUS

(75) Inventors: Thomas Patrick O'Connor, Westbrook, ME (US); Philip Andersen, Poland, ME (US); Randall Groat, Freeport, ME (US); Eugene Regis Krah, Yarmouth, ME (US); Jill Saucier, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 13/639,068

(22) PCT Filed: Apr. 1, 2011

(86) PCT No.: PCT/US2011/030945
§ 371 (c)(1),
(2), (4) Date: Dec. 19, 2012

(87) PCT Pub. No.: WO2011/123781
PCT Pub. Date: Oct. 6, 2011

(65) Prior Publication Data
US 2013/0101987 A1 Apr. 25, 2013

Related U.S. Application Data

(60) Provisional application No. 61/320,461, filed on Apr. 2, 2010.

(51) Int. Cl.
| | | |
|---|---|---|
| *G01N 33/53* | (2006.01) | |
| *G01N 33/68* | (2006.01) | |
| *C07K 16/10* | (2006.01) | |
| *C07K 14/005* | (2006.01) | |
| *G01N 33/569* | (2006.01) | |
| *G01N 33/577* | (2006.01) | |

(52) U.S. Cl.
CPC ........ *G01N 33/6854* (2013.01); *C07K 16/1045* (2013.01); *C07K 14/005* (2013.01); *G01N 33/56983* (2013.01); *C07K 2317/34* (2013.01); *G01N 33/56988* (2013.01); *G01N 33/577* (2013.01)
USPC ................ 435/7.93; 435/5; 435/7.1; 435/7.9; 435/7.92

(58) Field of Classification Search
CPC ..................... C12N 1/702; C12N 2740/15022; Y10S 530/826; Y10S 435/975; G01N 33/56983; G01N 33/56988; G01N 2333/155; G01N 2469/20; G01N 33/577; G01N 33/58; G01N 33/68; C07K 7/08; C07K 16/1045; C07K 2317/34
See application file for complete search history.

(56) References Cited

U.S. PATENT DOCUMENTS

| | | |
|---|---|---|
| 4,629,783 A | 12/1986 | Cosand |
| 4,879,212 A | 11/1989 | Wang et al. |
| 4,900,548 A | 2/1990 | Kitchen |
| 5,037,753 A | 8/1991 | Pedersen et al. |
| 5,118,602 A | 6/1992 | Pedersen et al. |
| 5,177,014 A | 1/1993 | O'Connor et al. |
| 5,219,725 A | 6/1993 | O'Connor et al. |
| 5,565,319 A | 10/1996 | Pedersen et al. |
| 5,576,177 A | 11/1996 | Fridland et al. |
| 5,591,572 A | 1/1997 | Kemp et al. |
| 5,627,026 A | 5/1997 | O'Connor et al. |
| 5,648,209 A | 7/1997 | Avrameas et al. |
| 5,656,732 A | 8/1997 | Anderen et al. |
| 5,705,331 A | 1/1998 | Arthur et al. |
| 5,726,010 A | 3/1998 | Clark |
| 5,726,013 A | 3/1998 | Clark |
| 5,736,378 A | 4/1998 | Elder et al. |
| 5,750,333 A | 5/1998 | Clark |
| 5,820,869 A | 10/1998 | Wasmoen et al. |
| 5,833,993 A | 11/1998 | Wardley et al. |
| 5,846,825 A | 12/1998 | Yamamoto |
| 5,849,303 A | 12/1998 | Wasmoen et al. |
| 6,015,565 A * | 1/1999 | Rose et al. ................. 424/229.1 |
| 5,994,516 A | 11/1999 | Pancino et al. |
| 6,077,662 A | 6/2000 | Compans et al. |

(Continued)

FOREIGN PATENT DOCUMENTS

| | | |
|---|---|---|
| EP | 0 602 046 | 11/1997 |
| EP | 0 887 412 | 12/1998 |
| EP | 0 962 774 | 12/1999 |
| JP | 02-11524 | 1/1990 |
| JP | 07-159408 | 6/1995 |
| WO | WO 90/06510 | 6/1990 |
| WO | WO 90/13573 | 11/1990 |
| WO | WO 92/09632 | 6/1992 |
| WO | WO 92/22573 | 12/1992 |
| WO | WO 93/01304 | 1/1993 |

(Continued)

OTHER PUBLICATIONS

Pedersen, et al., "Isolation of a T-lymphotropic virus from domestic cats with an immunodeficiency-like syndrome", Science, 235:790 (1987).

(Continued)

*Primary Examiner* — Louise Humphrey
(74) *Attorney, Agent, or Firm* — McDonnell Boehnen Hulbert & Berghoff LLP (57) ABSTRACT

Method, device and kit for the detection of antibodies directed to Feline Immunodeficiency Virus (FIV). The method includes contacting the felid biological sample with FIV env polypeptide and detecting whether the polypeptide substantially binds to the antibody in the biological sample. The method will detect FIV antibodies in a sample from animals that have been naturally infected but the method will not detect antibodies in a sample from animals that have not been infected and that have not been vaccinated with an FIV vaccine after within about the previous five to eight weeks.

8 Claims, 5 Drawing Sheets

(56) References Cited

U.S. PATENT DOCUMENTS

| | | | |
|---|---|---|---|
| 6,228,608 | B1 | 5/2001 | Young et al. |
| 6,254,872 | B1 | 7/2001 | Yamamoto |
| 6,284,253 | B1 | 9/2001 | Barr et al. |
| 6,300,118 | B1 | 10/2001 | Chavez et al. |
| 6,331,616 | B1 | 12/2001 | Tompkins et al. |
| 6,383,765 | B1 | 5/2002 | Andersen et al. |
| 6,391,304 | B1 | 5/2002 | Richardon et al. |
| 6,447,993 | B1 | 9/2002 | Yamamoto |
| 6,455,265 | B1 | 9/2002 | Serres |
| 6,458,528 | B1 * | 10/2002 | Groat et al. .......... 435/5 |
| 6,503,713 | B1 | 1/2003 | Rana |
| 6,544,528 | B1 | 4/2003 | Yamamoto |
| 6,613,530 | B1 | 9/2003 | Wienhues et al. |
| 6,667,158 | B1 | 12/2003 | Bavari et al. |
| 6,667,295 | B1 | 12/2003 | Deng |
| 7,201,903 | B2 | 4/2007 | Groat et al. |
| 7,285,278 | B2 | 10/2007 | Groat et al. |
| 7,291,338 | B2 | 11/2007 | Groat et al. |
| 7,335,360 | B2 | 2/2008 | Groat et al. |
| 7,348,136 | B2 | 3/2008 | Groat et al. |
| 7,776,546 | B2 | 8/2010 | Groat et al. |
| 2004/0096460 | A1 | 5/2004 | Deng |
| 2004/0110284 | A1 | 6/2004 | Bavari et al. |
| 2004/0115621 | A1 | 6/2004 | Rodrigo et al. |
| 2005/0058992 | A1 | 3/2005 | Groat et al. |
| 2005/0058993 | A1 | 3/2005 | Groat et al. |
| 2006/0002957 | A1 | 1/2006 | Groat et al. |
| 2006/0003445 | A1 | 1/2006 | Groat et al. |
| 2006/0004184 | A1 | 1/2006 | Groat et al. |
| 2006/0205923 | A1 | 9/2006 | Groat et al. |
| 2009/0196872 | A1 | 8/2009 | Kato et al. |

FOREIGN PATENT DOCUMENTS

| | | |
|---|---|---|
| WO | WO 94/02612 | 2/1994 |
| WO | WO 94/06471 | 3/1994 |
| WO | WO 96/40268 | 12/1996 |
| WO | WO 96/40953 | 12/1996 |
| WO | WO 96/40956 | 12/1996 |
| WO | WO 96/40957 | 12/1996 |
| WO | WO 97/07817 | 3/1997 |
| WO | WO 99/29182 | 6/1999 |
| WO | WO 01/04280 | 1/2001 |
| WO | WO 03/015814 | 2/2003 |
| WO | WO 2004/100985 | 11/2004 |

OTHER PUBLICATIONS

Talbott, et al., "Nucleotide sequence and genomic organization of feline immunodeficiency virus", Proc. Natl. Acad. Sci., 86:5743-5747 (1989).

Olmsted et al., "Molecular cloning of feline immunodeficiency virus", Proc. Natl. Acad. Sci., 86:2448-2452 (1989).

Phillips, et al., "Comparison of Two Host Cell Range Variants of Feline Immunodeficiency Virus", Journal of Virology, 64:4605-4613 (1990).

Miyazawa, et al., "Preliminary comparisons of the biological properties of two strains of feline immunodeficiency virus (FIV) isolated in Japan with FIV Petaluma strain isolated in the United States", Arch Virol., 108:59-68 (1989).

Morikawa, et al., "Identification of conserved and variable regions in the envelope glycoprotein sequences of two feline immunodeficiency viruses isolated in Zurich, Switzerland", Virus Research, 21:53-63 (1991).

Moraillon, et al., "In vitro properties and experimental pathogenic effect of three strains of feline immunodeficiency viruses (FIVE) isolated from cats with terminal disease", Veterinary Microbiology, 31:41-54 (1992).

Yamamoto, et al., "Pathogenesis of experimentally induced feline immunodeficiency virus infection in cats", Am. J. Vet. Res., 49:1246-1258 (1988).

Pacino, et al., "B Epitopes and Selection Pressures in Feline Immunodeficiency Virus Envelope glycoproteins", Journal of Virology, 67:664-672 (1993).

Erdenbaatar, et al., Enzyme-Linked Immunosorbent assay to differentiate the Antibody responses of Animals Infected with Brucella Species from Those of Animals Infected with Yersinia enterocolitica 09, Cinical and Diagnostic laboratory Immunology, 10:710-714 (2003).

Maki, N. et al. "Molecular Characterization and Heterogeneity of Feline Immunodeficiency Virus Isolates", Archives of Virolology, 1992, vol. 123, pp. 29-45.

Yamamoto, J.K. et al., "Experimental Vaccine Protection against Homologous and Heterologous Strains of Feline Immunodeficiency Virus", Journal of Virology, 1993, vol. 67, No. 1, pp. 601-605.

Hohdatsu, T. T et al., "Effect of Dual-subtype Vaccine Against Feline Immunodeficiency Virus Infection", Veterinary Microbiology, 1997, vol. 58, pp. 155-165.

Uhl, E.W. et al., "FIV Vaccine Development and its Importance to Veterinary and Human Medicine: A Review FIV Vaccine 2002 Update and Review", Veterinary Immunology and Immunopathology, 2002, vol. 90, pp. 133-132.

Murray, D.M., "Identifying FIV Vaccinates", Journal of the American Veterinary Medical Association, 2003, vol. 222, p. 710.

Moon, D., "Another Solution to Identify FIV-Vaccinated Cats", Journal of the American Veterinary Medical Association, 2003, vol. 22, No. 9, p. 1207.

Calandrella, M., "Desitometric Analysis of Western Blot Assays for Feline Immunodeficiency Virus Antibodies", Veterinary Immunology and Immunopathology, 2001, vol. 79, pp. 261-271.

Hartmann, K. et al., "Comparison of Six In-House Tests for the Rapid Diagnosis of Feline Immunodeficiency and Feline Leukemia Virus Infections", The Veterinary Record, 2001, vol. 149, pp. 317-320.

Richardson, J., et al., "Delayed Infection after Immunization with a peptide from the Transmembrane Glycoprotein of the Feline Immunodeficiency Virus", Journal of Virology, 1998, vol. 72, pp. 2406-2415.

Finerty, Susan, et al., "Mucosal immunization with experimental feline immunodeficiency virus (FIV) vaccines induces both antibody and T cell responses but does not protect against rectal FIV challenge", Vaccine, 2000, vol. 18, pp. 3254-3265.

DeRonde, Anthony, et al., "Antibody Response in Cats to the Envelope Proteins of Feline Immunodeficincy Virus: identification of an Immunodominant Neutralization Domain", Virology, 1994, vol. 198, pp. 257-264.

Lombardi, Stefania, et al., "Identification of a Linear Neutralization Site within the Third Variable region of the Feline Immunodeficiency Virus Envelope", Journal of Virology, 1993, vol. 67, pp. 4742-4749.

Avrameas, A., et al., "Localisation of Three Epitopes of the ENV Protein of Feline Immunodeficiency Virus", Molecular Immunology, 1992, vol. 29, pp. 565-572.

Avrameas, A., et al., "Serological Diagnosis of Feline Immunodeficiency Virus Infection Based on Synthetic Peptides from Env Glycoproteins", Res. Virol, 1993, vol. 144, pp. 209-218.

Olmsted, Robert , "Nucleotide Sequence Analysis of Feline Immunodeficiency Virus: Genome Organization and Relationship to Other Lentiviruses", Proc. Natl. Acad. Sci. USA, 1989, vol. 86, pp. 8088-8092.

Gallaher, William, et al., "A General Model for the Transmembrane Proteins of HIV and Other Retroviruses", AIDS Research and Human Retroviruses, 1989, vol. 5, pp. 431-440.

Mermer, B., et al., "Similarities Between the Transmembrane Proteins of FIV and HIV", Abstract distributed on and Poster Presentation during the Cold Spring Harbor Conference, 1991.

Javaherian, et al., "Principal neutralizing domain of the human immunodeficiency virus type 1 envelope protein", Proc. Natl. Acad. Sci. USA, 1989, vol. 86, pp. 6768-6772.

Steinman, et al., "Biochemical and Immunological Characterization of the Major Structural Proteins of Feline Immunodeficiency Virus", Journal of General Virology, 1990, vol. 71, pp. 701-706.

Gnann, et al, "Fine Mapping of an Immunodominant Domain in the Transmembrane Glycoprotein of Human Immunodeficiency Virus", Journal of Virology, 1987, vol. 61, pp. 2639-2641.

Chong, et al., "Analysis of Equine Humoral Immune Responses to the Transmembrane Envelope Glycoprotein (gp45) of Equine Infectious Anemia Virus", Journal of Virology, 1991, pp. 1013-1018.

(56) References Cited

OTHER PUBLICATIONS

Berton, et al. "The Antigenic Structure of the Influenza B Virus Hemagglutinin: Operational and Topological Mapping with Monoclonal Antibodies", Virology, 1985, vol. 143, pp. 583-594.

Mermer, et al., "A Recombinant-based Feline Immunodeficiency Virus Antibody Enzyme-Linked Immunosorbent Assay", Veterinary Immunology and Immunopathology, 1992, vol. 35, pp. 133-141.

Massi, et al., "Most Potential Linear B Cell Epitopes of Env Glycoproteins of Feline Immunodeficiency Virus are Immunogenically Silent in Infected Cats", AIDS Research and Human Retroviruses, 1997, vol. 13, pp. 1121-1129.

Lutz, et al., "FIV Vaccine Studies I, Immune Response to Recombinant FIV ENV Gene Products and Outcome After Challenged Infection", Veterinary Immunology and Immunopathology, 1995, vol. 46, pp. 103-113.

Tijhaar, Edwin, et al., "*Salmonella typhimurium* AroA Recombinants and Immune-stimulating Complexes as Vaccine Candidates for Feline Immunodeficiency Virus", Journal of General Virology, 1997, vol. 78(12), pp. 3265-3275.

Fort Dodge Animal Health, First Feline Aids Vaccine Available, Press Release, Aug. 12, 2002.

Fel-O-Vax® FIV Product Brochure, 2002 Fort Dodge Animal Health.

Wimley, William, et al., Designing Transmembrane $\alpha$-Helices that insert Spontaneously, Biochemistry, 29:4432-4442 (2000).

Ponsati, Berta, et al., "A Synthetic Strategy for Simulatenous Purification-Conjugation of Antigenic Peptides", analytical Biochemistry, 181:389-395 (1989).

Rimmelzwaan, G.F., et al., "gag-And env-specific serum antibodies in cats after natural and experimental infection with feline immunodeficincy virus", Veterinary Microbiology, 39:153-165 (1994).

Calzolari, et al., "Serological diagnosis of feline immunodeficiency virus infection using recombinant transmembrane glycoprotein", Veterinary Immunology and Immunopathology, 46:83-92 (1995).

\* cited by examiner

FIG. 1A

| | | | | | | | | | | | |
|---|---|---|---|---|---|---|---|---|---|---|---|
| E | L | G | C | N | Q | N | Q | F | F | C | K | SEQ ID NO:1
| A | L | G | C | N | Q | N | Q | F | F | C | K | SEQ ID NO:2
| A | A | G | C | N | Q | N | Q | F | F | C | K | SEQ ID NO:3
| E | A | A | C | N | Q | N | Q | F | F | C | K | SEQ ID NO:4
| E | L | A | C | A | Q | N | Q | F | F | C | K | SEQ ID NO:5
| E | L | G | C | A | A | N | Q | F | F | C | K | SEQ ID NO:6
| E | L | G | C | N | A | A | Q | F | F | C | K | SEQ ID NO:7
| E | L | G | C | N | Q | A | A | F | F | C | K | SEQ ID NO:8
| E | L | G | C | N | Q | N | A | A | F | C | K | SEQ ID NO:9
| E | L | G | C | N | Q | N | Q | A | A | C | K | SEQ ID NO:10
| E | L | G | C | N | Q | N | Q | F | A | C | A | SEQ ID NO:11
| E | L | G | C | N | Q | N | Q | F | F | C | A | SEQ ID NO:12

DETECTION OF FELINE IMMUNODEFICIENCY VIRUS

CROSS REFERENCE TO RELATED APPLICATION

This application claims benefit of U.S. Provisional Application No. 61/320,461, filed Apr. 2, 2010, which is incorporated herein by reference in its entirety.

SEQUENCE LISTING STATEMENT

The sequence listing is filed in this application in electronic format only and is incorporated by reference herein. The sequence listing text file "09-032-WO_SEQLIST.txt" was created on Mar. 29, 2011, and is 3,191 bytes in size.

FIELD OF THE INVENTION

The invention is related to the detection of Feline Immunodeficiency Virus (FIV). More particularly, the invention is directed to a method for detecting FIV in naturally infected animals, but not in animals that have been vaccinated with an FIV vaccine.

BACKGROUND OF THE INVENTION

Feline immunodeficiency virus (FIV), formerly called feline T-lymphotrophic lentivirus, was first isolated in 1986 from a large multiple cat household in Petaluma, Calif. (Pederson et al., Science (1987) 235:790). HIV infects cats to produce an AIDS-like syndrome. Although FIV is morphologically and pathologically similar to the human immunodeficiency virus (HIV), it has been shown to be antigenically distinct from HIV. Like HIV, once a cat becomes infected with FIV, the disease progresses from a primary infection (viremia, fever, general lymphadenitis) to a lengthy asymptomatic phase, followed by severe impairment in immune function caused by a reduction in CD4 lymphocytes, and resulting in heightened susceptibility to secondary infections and ultimately death.

FIV has been classified as a member of the subfamily Lentiviridae in the family Retroviridae, the family that includes human and simian immunodeficiency viruses, equine infectious anaemia, maedi visna of sheep and caprine arthritis encephalitis viruses (CAEV). The genome of FIV is organized like other lentiviruses with three long open reading frames corresponding to gag, pol and env (Talbott et al., Proc. Natl. Acad. Sci. (1989) 86:5743; Olmsted et al., Proc. Natl. Acad. Sci. (1989) 86:2448). The gag gene codes for the major structural components of the virus, the env gene codes for the envelope glycoprotein, and the pol gene codes for the polymerase protein.

The gag gene is expressed as a 55 kD polyprotein that is processed into three subunits: a p15 matrix protein, a p24 capsid protein, and a p10 nucleocapsid protein. The pol gene encodes three proteins: the protease, reverse transcriptase and a p14.6 protein of unknown function. Autoprocessing by the protease portion of the gene gives rise to all three proteins of the pol region. Additionally, the protease is responsible for the processing of the gag precursor. The pol gene is expressed as a gag pol fusion protein. The envelope gene is expressed as a 160 kD glycoprotein, gp160. The antigenicity of the FIV core proteins is similar to other lentiviruses.

Several independent viral isolates have been prepared across the world, and a certain number of studies have been carried out in order to demonstrate the structure of the isolated strains: the American strain Petaluma, Talbott et al. Natl. Acad. Sci. USA, 1989, 86, 5743-5747; Philipps et al., J. Virol., 1990, 64, 10, 4605-4613), the Japanese strains (the TM1 and TM2 strains), Miyazawa et al., Arch. Virol., 1989, 108, 59-68, and the Swiss isolates (FIVZ1 and FIVZ2), Morikawa et al., Virus Research, 1991, 21, 53-63.

The nucleotide sequences of three proviral clones derived from American FIV isolates (Petaluma strain) have been described (clones FIV34TF10, FIV14 and isolate PPR) (Olmsted, et al. 1989; Philipps et al., 1990; Talbott et al., 1989) and compared with two Swiss isolates (Morikawa et al. 1991). This comparison led Morikawa et al. to specify the presence of certain conserved regions and certain variable regions within the env gene of FIV. French strains have also been isolated (strains Wo and Me) (Moraillon et al., 1992, Vet. Mic., 31, 41-45).

The virus replicates optimally in blood mononuclear cells and has a tropism for T-lymphocytes, peritoneal macrophage, brain macrophage and astrocytes. In common with other retroviruses, the genetic material of FIV is composed of RNA and the production of a DNA copy of the viral RNA is an essential step in the replication of FIV in the host. This step requires the enzyme reverse transcriptase that is carried into the host by the invading virus. The DNA version of the viral genome is inserted into the genetic material of infected host cells in which it continues to reside as a provirus. This provirus is replicated every time the cell divides and can code for the production of new virus particles. Cells infected with FIV remain infected for the duration of their lifespan.

The virus appears to be spread naturally by horizontal transmission, predominantly by bite wounds from an infected cat as these animals shed appreciable amounts of virus in saliva (Yamamoto et al., Am. J. Vet. Res. 1988, 8:1246). Vertical transmission has been reported, but is rare.

Detecting natural FIV infection has become prevalent as FIV infection is widespread worldwide. Current diagnostic screening tests for HIV infection detect serum antibody to FIV. A number of diagnostic tests are commercially available. For example, PETCHEK® FIV Ab test kit (IDEXX Laboratories, Westbrook, Me.) is an immunoassay based diagnostic test for HIV infection. Virus detection kits are also available but not as prevalent.

Also, as vaccines have been developed in attempt to combat the disease, it has become important to be able to discriminate between vaccinated cats versus naturally infected cats. However, currently available screening tests do not allow for accurate differentiation between vaccinated animal and naturally infected animals.

Recently, various techniques have been developed to distinguish vaccinated from infected animals. See, e.g., US 2006/0003445 and US 2005/0058993. While these techniques are accurate and effective, the inventors have recognized that further improvements in the methods may be useful to enhance the commercial success of the products associated with the methods.

SUMMARY OF THE INVENTION

In one aspect, the invention is directed to a method for detecting antibodies to Feline Immunodeficiency Virus (FIV) in a biological sample. The method includes contacting the biological sample with the FIV env polypeptide of SEQ ID NO:1 (ELGCNQNQFFCK) and a monoclonal antibody that binds to SEQ ID NO:1, and detecting whether antibodies in the sample compete with the monoclonal antibody for binding to SEQ ID NO:1, thereby determining that the sample contains antibodies to FIV. In the method, FIV antibodies in a sample from animals that have been naturally infected will compete with the monoclonal antibody for binding to SEQ ID NO: 1 but antibodies in a sample from animals that have not been infected or animals that have been vaccinated against FIV more than five to eight weeks prior to the sample being obtained will not compete with the monoclonal antibody for binding to SEQ ID NO: 1.

Further and alternatively, the method can include distinguishing between (a) felids that have been naturally infected with FIV, (b) felids that have been vaccinated with an FIV vaccine, and (c) non-vaccinated, non-infected felids. If antibodies in the sample compete with the monoclonal antibody for binding to SEQ ID NO: 1, it can be determined that the animal has not been infected with FIV or may have been vaccinated with an FIV vaccine. If antibodies in the sample compete with the monoclonal antibody for binding to SEQ ID NO: 1, the method can be repeated after about five weeks and it can be determined that (i) the felid is naturally infected if antibodies in the sample compete with the monoclonal antibody for binding to SEQ ID NO: 1, or (ii) the felid has not been infected and has been vaccinated with an FIV vaccine if antibodies in the sample compete with the monoclonal antibody for binding to SEQ ID NO: 1.

In particular aspects of the invention, competition between an FIV antibody the sample and the monoclonal antibody is identified when a signal associated with the binding of the monoclonal antibody to SEQ ID NO:1 in the presence of the antibody in the sample is less than about 25-50% of a signal associated with the binding of the monoclonal antibody to SEQ ID NO:1 in the absence of the antibody in the sample.

In another aspect, the invention is directed to a method for detecting antibodies to Feline Immunodeficiency Virus (FIV) in a biological sample. The method includes contacting the biological sample with the FIV env polypeptide of SEQ ID NO:1 (ELGCNQNQFFCK) and a monoclonal antibody that binds to SEQ ID NO:1, and detecting whether the polypeptide substantially binds to an antibody in the sample, thereby determining that the biological sample contains antibodies to FIV. In various aspects of the invention, the method will detect FIV antibodies in a sample from animals that have been naturally infected with FIV but the method will not detect antibodies in a sample from animals that have not been infected and have been vaccinated against FIV after about five to eight weeks from vaccination. Further and alternatively, if antibodies in the sample do not bind to the polypeptide, the method may determine that the animal has not been infected with FIV or may have been vaccinated with an FIV vaccine. If antibodies in the sample bind to the polypeptide, the method can be repeated after about five weeks and it can be determined either that (i) the felid is naturally infected if antibodies in the sample bind to the polypeptide, or (ii) the felid has not been infected and has been vaccinated with an FIV vaccine if antibodies in the sample do not bind to the polypeptide.

In a further aspect, the invention is directed to a method for detecting an HIV infection or vaccination status of a felid. The method includes contacting a biological sample provided by the felid and a monoclonal antibody that binds to SEQ ID NO:1 with a solid phase having SEQ ID NO:1 immobilized thereon, wherein the monoclonal antibody includes a label. The solid phase is washed to remove unbound reagents and the presence of the label at the solid phase is detected. The presence of the label indicates that the feline has not been infected with FIV, and the absence of the label indicates that the felid has been infected with FIV or the felid has been vaccinated with an FIV vaccine within about the prior five to eight weeks. Further and alternatively, the invention includes repeating the method after about five weeks for a felid providing a sample that indicates that the felid has been infected with FIV or has been vaccinated with an FIV vaccine, wherein the presence of the label indicates that the felid has been vaccinated with an FIV vaccine and the absence of the label indicates that the feline has been infected with FIV.

Still further, the invention is directed to a method for detecting antibodies to Feline Immunodeficiency Virus (FIV) in a biological sample. The method includes contacting the biological sample with the FIV env polypeptide of SEQ ID NO:1 (ELGCNQNQFFCK) and a monoclonal antibody that binds to SEQ ID NO:1, and detecting whether antibodies in the sample compete with the monoclonal antibody for binding to SEQ ID NO:1, thereby determining that the sample contains antibodies to FIV. In this aspect of the invention, FIV antibodies in a sample from animals that have been naturally infected will compete with the monoclonal antibody for binding to SEQ ID NO: 1 but with antibodies in a sample from animals that have not been infected or animals that have been vaccinated against FIV more than five to eight weeks prior to the sample being obtained will not compete with the monoclonal antibody for binding to SEQ ID NO: 1. In addition and alternatively, the method includes distinguishing between (a) felids that have been naturally infected with FIV, (b) felids that have been vaccinated with an FIV vaccine, and (c) non-vaccinated, non-infected felids.

In yet another aspect, the invention is directed to a kit for detecting FIV. The kit includes a dry porous carrier having immobilized thereon a FIV polypeptide of SEQ ID NO:1 and a monoclonal antibody that binds to SEQ ID NO:1.

In all of the aspects of the invention, the FIV env polypeptide may be bound to a solid phase. Also, the monoclonal antibody may be a monoclonal antibody produced by one of the hybridoma cell lines having ATCC deposit No. HB10295 (2F11) and ATCC deposit No. PTA-10050 (1C9). In other aspects, the monoclonal antibody may be a monoclonal antibody that recognizes the same epitope recognized by the monoclonal antibody produced by one of the hybridoma cell lines having ATCC deposit No. HB10295 (2F11) and ATCC deposit No. PTA-10050 (1C9).

DETAILED DESCRIPTION OF THE INVENTION

Before describing the present invention in detail, a number of terms will be defined. As used herein, the singular forms "a," "an", and "the" include plural referents unless the context clearly dictates otherwise.

As used herein, the term "polypeptide" refers to a compound of a single chain of amino acid residues linked by peptide bonds. The chain may be of any length. A protein is a polypeptide and the terms are used synonymously. The polypeptide is capable of binding one or more antibodies specific to different epitopes of the FIV polypeptide.

For the current invention, a suitable FIV env polypeptide for use in detecting FIV antibodies is ELGCNQNQFFCK [SEQ ID NO:1]. SEQ ID NO:1 is the sequence of native FIV env (amino acids 696-707). For the purposes of this application, SEQ ID NO:1 is also referred to as known as "IRG2 polypeptide" or simply "IRG2." SEQ ID NO:1 may also include an N-terminal cysteine residue in order to simplify the conjugation of SEQ ID NO:1 to a solid support.

A monoclonal antibody refers to an antibody specific to the FIV env polypeptide and exogenously introduced into a biological sample or immunological assay to detect FIV. In one aspect, the antibodies of the invention are monoclonal antibodies produced by a mouse myeloma cell line. This cell line can be made by fusing a mouse myeloma cell line with the spleen cells from mice that have been injected with the complete FIV env protein, or antigenic portion thereof. As more completely described in the examples below, two such cell lines have been deposited with the American Type Culture Collection (ATCC), 10801 University Boulevard, Manassas, Va. One monoclonal antibody useful in the current invention is produced from one of the hybridoma cell lines having ATCC deposit No. PTA-HB10295 (deposited Nov. 7, 1989), known as "anti-FIV env 2F11" or simply "2F11" (see U.S. Pat. No. 5,177,014, which is incorporated herein by reference in its entirety), and PTA-10050, known as "anti-FIV env 1C9" or simply "1C9" (deposited May 21, 2009).

The deposits will be maintained under the terms of the Budapest Treaty on the International Recognition of the Deposit of Microorganisms. The deposits are provided as a convenience to those of skill in the art and are not an admission that the deposit is required under 35 U.S.C. §112.

Figure 1A:
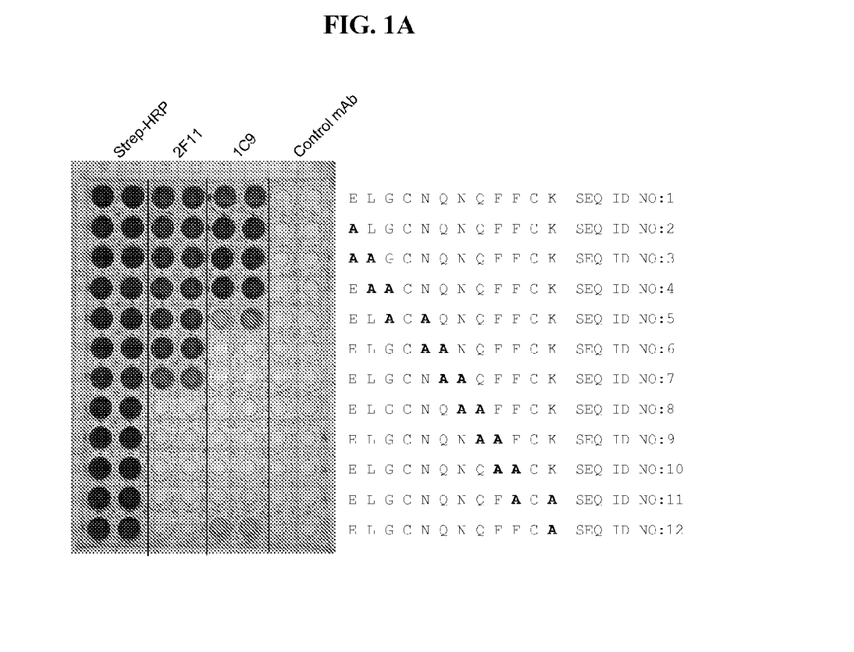
FIG. 1A is a photograph of a microtiter plate showing the results of an alanine mutagenesis experiment to determine the epitope for binding of 2F11 and 1C9 monoclonal antibodies to SEQ ID NO:1.
Figure 1B:
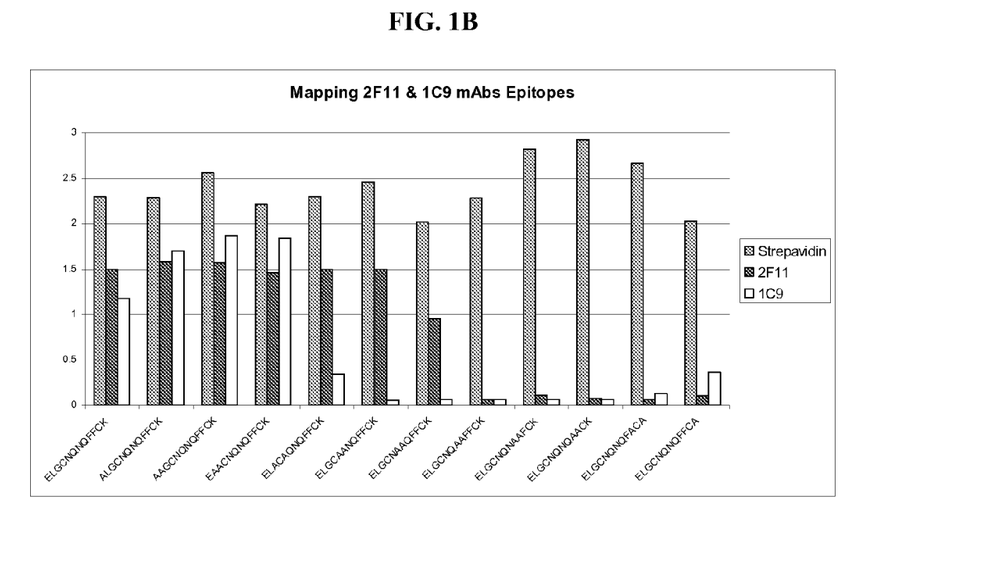
FIG. 1B is a graph showing the results of the screen of FIG. 1A.

An "epitope" is the antigenic determinant on the FIV env polypeptide that is recognized for binding by a paratope on antibodies specific to the FIV env polypeptide. Antibody 2F11 and antibody 1C9 bind to the IRG2 polypeptide at overlapping, but not identical, epitopes of the IRG2 polypeptide. FIG. 1 shows the results of an alanine mutagenesis screen of the IRG2 polypeptide. As described more fully in the examples below, the results of the screen show that the 2F11 monoclonal antibody specifically binds to the C-terminal region of SEQ ID NO:1 more specifically to amino acids including NQFFCK and the C-terminal lysine of SEQ ID NO:1. 1C9 monoclonal antibody binds to a second, epitope of SEQ ID NO:1, more specifically amino acids including CNQNQFFC and the C-terminal lysine of SEQ ID NO:1.

The term "label," as used herein, refers to a detectable compound, composition, or solid support, which can be conjugated directly or indirectly (e.g., via covalent or non-covalent means, alone or encapsulated) to a monoclonal antibody. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current invention could be, but is not limited to: alkaline phosphatase; glucose-6-phosphate dehydrogenase ("G6PDH"); horseradish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptavidin, digioxigenin, maltose, oligohistidine, 2,4-dinitrobenzene, phenylarsenate, ssDNA, dsDNA, and the like). The utilization of a label produces a signal that may be detected by means such as detection of electromagnetic radiation or direct visualization, and that can optionally be measured.

The monoclonal antibody can be linked to a label using methods well known to those skilled in the art. E.g., Immunochemical Protocols; Methods in Molecular Biology, Vol. 295, edited by R. Burns (2005)). The detectable monoclonal antibody conjugate may be used in a competitive assay format to generate a signal that is related to the presence or amount of an FIV-specific antibody in a test sample.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted to distinguish specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g, an immunohistochemical assay, an enzyme-linked immunosorbent assay (ELISA), a radioimmunoassay (RIA), or a western blot assay.

Animals infected with FIV are felids, which is to be understood to include all members of the order Felidae, including domestic cats, lions, tigers, jaguars, leopards, puma, ocelots, etc. As used herein, the terms "felid," "feline," "cat," or "animal" is a reference to all felids.

A "biological sample" refers to a sample from an animal subject including saliva, whole blood, serum, plasma or other sample known to contain FIV antibodies. A biological sample can be collected and stored by any convenient means that does not impact the ability of the sample to be tested in the method of the invention. Samples for use in the method of the invention may require preparation prior to use in the method. For example, samples may need to be precipitated, diluted, filtered or centrifuged to remove unwanted components or components may be added to the sample such as salts, detergents or additional proteins.

The term "solid support" or "solid phase" refers to a non-aqueous matrix to which an FIV polypeptide can adhere by covalent or non-covalent binding. Examples of solid support include supports formed partially or entirely of glass (e.g., controlled pore glass), synthetic and natural polymers, polysaccharides (e.g., agarose), polyacrylamides, polystyrene, polyvinyl alcohols and silicones, magnetic particles, latex particles, chromatographic strips, microtiter polystyrene plates, or any other substances that will allow bound antigens to be washed or separated from unbound materials. In certain embodiments, depending on the application, the solid support can be the well of an assay plate or can be a purification column (e.g., an affinity chromatography column).

Turning now to the various aspects of the invention, one aspect the invention is directed to an immunological method, devices and kits for detecting the presence of an amount of anti-FIV env antibody in a biological sample from a felid. The method can be used to determine whether a felid is infected with FIV or whether a felid has not been infected with FIV regardless of whether the felid has been vaccinated or has not been vaccinated with an FIV vaccine. For example, whether the felid has been vaccinated or not been vaccinated with a whole-killed FIV vaccine after a period of time, e.g. within five to eight weeks post vaccination.

In one embodiment, the invention is directed to a competitive immunoassay for detection of anti-FIV env antibodies. In particular, a biological sample from a felid, potentially containing anti-FIV env antibodies, is contacted with a FIV env polypeptide conjugated to a solid phase and sequentially or simultaneous with a monoclonal antibody conjugated to a detectable label. The anti-FIV env antibodies of interest, present in the sample, compete with the monoclonal antibody conjugated to a detectable label for binding with the FIV env polypeptide conjugated to a solid phase. The amount of the label associated with the solid phase can be determined after separating unbound antibodies and the solid phase. The amount of the signal obtained from the label is inversely related to the amount of FIV env antibody of interest present in the sample.

In one particular embodiment of the invention, the immunoassay for diagnosing FIV may be carried out with the IRG2 polypeptide as the solid phase reagent. A monoclonal antibody that binds to the IRG2 polypeptide and that is conjugated to a label is contacted with the solid phase along with the sample from a felid. If the sample contains anti-FIV env antibodies, the antibodies will bind to the polypeptide on the solid phase and prevent the binding of the labeled monoclonal antibody. In other words, the labeled monoclonal antibody will only bind to the epitope on the FIV env polypeptide if the anti-FIV env antibodies of the biological sample do not saturate all the FIV env polypeptide bound to the solid phase. Accordingly, if the labeled monoclonal antibody conjugates of the invention bind to the FIV env polypeptide, the results are indicative of the absence of anti-FIV env antibodies. In various embodiments of the invention, the monoclonal antibody is either 2F11 or 1C9.

In various aspects of the invention, the method will detect antibodies to FIV env in felids that have been naturally infected, but not from felids that have been vaccinated with an FIV vaccine five to eight weeks following vaccination. Vaccines for FIV are described, for example, in U.S. Pat. Nos. 6,667,295, 5,833,993, 6,447,993, 6,254,872 and 6,544,528, and published U.S. Patent Application 20040096460, each of which is incorporated herein by reference in their entirety. U.S. Pat. Nos. 6,447,993 and 6,254,872, incorporated herein by reference in their entirety, describe vaccines that are prepared from cell free-viral isolates of different FIV subtypes or a combination of cell lines each infected with different prototype FIV virus from a different subtype. U.S. Pat. No. 5,833,933 describes vaccines containing DNA sequences encoding FIV gag protein and FIV env protein. These vaccines include an expression system for expressing the sequences. One available vaccine is FEL-O-VAX® FIV vaccine (Fort Dodge Animal Health, Overland Park, Kans.). FEL-O-VAX® vaccine is manufactured from the whole FIV virus that is inactivated with formaldehyde. Vaccination with FEL-O-VAX® vaccine is subcutaneous and three doses are recommended at two to three week intervals.

In some instances, during an initial phase following a vaccination, an animal may temporarily (transiently) produce lower levels of certain antibodies to specific FIV polypeptides that are elements of a vaccine, as compared the levels of antibodies produced in response to a natural infection. Certain antibodies produced against polypeptides of the vaccine taper off after a period of time to the point that antibody to these polypeptides is not detected after the initial phase.

For example, the inventors recognized that a fraction of animals test seropositive for FIV antibodies against the IRG2 polypeptide (SEQ ID NO:1) for about five to eight weeks after vaccination with the FEL-O-VAX® vaccine. However, animals so vaccinated do not generate persistent levels of antibodies against the FIV env polypeptide after about five to eight weeks from completion of vaccination.

The differences in the immune response between animals that are vaccinated and animals that are naturally infected provide a means for determining whether an animal has been vaccinated or is naturally infected. Using the method of the invention, animals that have been naturally infected with FIV can be distinguished from animals that have not been infected or have been vaccinated against an HIV infection.

Given that the production of detectable antibodies that are directed toward IRG2 usually drops off after about eight weeks from completion of vaccination, in one aspect of the invention the biological sample is obtained from the animal that has not received an FIV vaccine within eight weeks of vaccination. If the vaccination status is unknown and the test indicates infection (based on a reaction with the antibody capture protein), a retest after an additional five to eight weeks can be recommended.

Accordingly, the absence of antibodies to the IRG2 polypeptide in a sample indicates that the cat is not naturally infected with FIV or has not been vaccinated against FIV within eight weeks of testing. Conversely, however, if the monoclonal antibody conjugates of the invention do not bind to the FIV env polypeptide, this is indicative of the presence of anti-FIV env antibodies, and that the cat is naturally infected with FIV or has been vaccinated within the previous eight weeks. As typical with competitive assays, the signal generated from the conjugated label indicates that no antibodies are present in the sample. To the extent that a quantitative analysis is helpful, the amount of the signal will be inversely proportional to the amount of anti-FIV env antibodies present in the sample.

The monoclonal antibody for use in the invention includes the monoclonal antibodies that bind to the IRG2 polypeptide. For example, the 2F11 and 1C9 monoclonal antibodies bind to the IRG2 polypeptide. In addition, monoclonal antibodies that bind the epitopes on the IRG2 polypeptide that bind 2F11 and 1C9, i.e., antibodies that compete with 2F11 or 1C9 for binding to IRG2, may be used.

Binding of the monoclonal antibody to the IRG2 polypeptide provides a detectable antibody/peptide complex. The complex can be detected by methods well known to those of skill in the art. For example, when the IRG2 polypeptide is bound to a solid support, and the monoclonal antibody is conjugated to a label, the formation of the complex will result in the label becoming bound to the support after the support is washed of unbound reagents. The presence of the label on the support can be determined and/or quantitated.

In one aspect, binding of an antibody in a biological sample from a felid to the IRG2 polypeptide is determined when competition between a sample antibody and either the 2F11 or 1C9 monoclonal antibody for binding to the polypeptide is detected. Competition can be detected when the amount of a signal associated with the binding of the either the 2F11 or 1C9 monoclonal antibody to the polypeptide is less than a percentage (cut off value) of the amount of a signal associated with the binding of the monoclonal antibody in the absence of antibodies in the sample (e.g., negative control). In various embodiment of the invention, the cut off value is between 25% and 50%, and more particularly 40%. Therefore, sample antibody is detected when the signal detected is less than about 50%, about 40%, about 30% or about 25% of the signal detected from a negative control.

In various embodiments of the invention, the FIV env polypeptide is immobilized on a solid phase, such as a microtiter well or a porous matrix of a lateral flow device Immobilization the FIV env polypeptide onto a device or solid phase is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

In one particular embodiment, the invention uses a lateral flow device such as the SNAP® immunoassay device (IDEXX Laboratories), or a device as described in U.S. Pat. No. 5,726,010, which is incorporated herein by reference in its entirety.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

Polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain (Merrifield, 1963, J. Am. Chem. Soc., 85:2149-2156). Recombinant proteins can also be used. These proteins may be produced by expression in cultured cells of recombinant DNA molecules encoding a desired portion of the FIV genome. The portion of the FIV genome may itself be natural or synthetic, with natural genes obtainable from the isolated virus by conventional techniques. Of course, the genome of FIV is RNA, and it will be necessary to transcribe the natural RNA into DNA by conventional techniques employing reverse transcriptase. Polynucleotides may also be synthesized by well-known techniques. For example, short single-stranded DNA fragments may be prepared by the phosphoramidite method described by Beaucage and Carruthers, 1981, Tett. Letters 22:1859-1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired FIV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the FIV DNA fragment encoding the desired polypeptide product, transcriptional and translational initiation regulatory sequences joined to the 5'-end of the FIV DNA termination regulatory sequences joined to the 3'-end of the fragment. The transcriptional regulatory sequences will include a heterologous promoter that is recognized by the host. Conveniently, a variety of suitable expression vectors are commercially available for a number of hosts.

To be useful in the detection methods of the present invention, the polypeptides are obtained in a substantially pure form, that is, typically from about 50% w/w or more purity, substantially free of interfering proteins and contaminants. Preferably, the FIV polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained.

The following are provided for exemplification purposes only and are not intended to limit the scope of the invention described in broad terms above. All references cited in this disclosure Pr are incorporated herein by reference.

EXAMPLES

Example 1

Screening of Samples for FIV Antibodies 124 feline blood serum samples were obtained from Port Charlotte Animal Welfare League, FL (PCAWL). The blood serum samples were pre-screened and determined as positive or negative for FIV by either: 1) an FIV plate assay coated with FIV p24 and polypeptide RPDFESEKCCNRWEWRPDFESEKSKSKSKSMQELGSNQNQFFSKV (SEQ ID NO:13 (see U.S. Pat. No. 7,201,903) (the "Aligned Assay") or; 2) by the IRG2 indirect assay as more fully described in US 2006/0003445, both of which in incorporated herein by reference in its entirety.

For the indirect IRG2 assays, the IRG2 peptide was synthesized at on outside vendor. Polypeptide stocks were prepared at 10 mg/ml in deionized water. The polypeptides were then coated on microplate wells (0.5 µg/ml in 50 mM sodium carbonate buffer, pH 9.6 (100 µl)). The plates were then blocked/overcoated with 2% Tween-20/2.5% sucrose, and allowed to dry in mylar bags with desiccant.

Serum samples were diluted 1:500 in a Tris based buffer containing non-specific proteins. The diluted samples were added to the microtiter plate wells (100 µL/well) and the plates were incubated at room temperature for 15 minutes. Following incubation, the microplates were washed with PBS/Tween. Commercially available goat anti-cat IgG:peroxidase conjugate (1:2000) diluted in a Tris based buffer containing non-specific proteins was added to the wells. The plates were incubated for another fifteen minutes at room temperature and washed a second time with PBS/Tween. Peroxidase substrate was added and the plates were incubated a third time for 10 minutes at room temperature. Peroxidase product (activity) was measured with a spectrophotometer (650 nm). The cutoff value used to determine positive sample results was >0.100 OD units.

The Aligned Assay was conducted as follows: Samples were added undiluted to microtiter plate wells (100 µL/well) and incubated 15 minutes at room temperature. Following incubation, the plate was washed with PBS-Tween buffer and an analyte specific conjugate was added to the plate (100 µL/well). The plates were incubated again for 15 minutes at room temperature and washed a second time with PBS-Tween buffer. Peroxidase substrate was added (100 µL/well) and the plates were incubated at third time for 15 minutes at room temperature. Peroxidase product (activity) was measured with a spectrophotometer (650 nm).

Sample results were calculated as S/P ratios: (Sample–NC)/(PC–NC). Samples are determined as positive based on a S/P cutoff of ≥0.50.

Table 1 shows a comparison of the results from the IRG2 indirect assay and results from the Aligned Assay described above.

TABLE 1

| N = 124 samples | Aligned Assay | IRG2 Indirect |
|---|---|---|
| Positive (+) | 80 | 80 |
| Negative (−) | 44 | 43 |
| Equivocal (+/−) | 0 | 1 |

Example 2

Production of Labeled Antibodies

The 2F11 and 1C9 monoclonal antibodies were isolated from the ATCC deposited cells lines as described herein. The 2F11 and 1C9 antibodies were conjugated to HRP using the heterobifunctional cross-linker succinimidyl 4-(N-maleimindomethyl) cyclohexane-1-carboxylate (SMCC) (Pierce) by standard methods.

Example 3

2F11 and 1C9 Competition Assays

The 124 feline serum samples screened in Example 1 were evaluated using the 2F11 antibody-based assay and the 1C9 antibody-based assay as outlined below. In each of these methods, the IRG2 polypeptide was coated onto the wells of a microtiter plate as described below.

2F11 MAb Competition Assay
IRG2 and IRG2:BSA Plate Coating Protocol:
Unconjugated IRG2 polypeptide and IRG2 polypeptide conjugated to Bovine Serum Albumin (BSA) were coated on microtiter plate (100 µl/well) wells (0.5 ug/mL for unconjugated IRG2 and 0.75 ug/mL for conjugated IRG2:BSA) in 0.05M Sodium Carbonate, pH 9.6. Following overnight incubation at room temperature, the plates were washed three times with PBS-Tween buffer. Protein binding sites on the microtiter plate wells were then blocked/overcoated with 2% Tween-20/2.5% Sucrose (300 µL/well). The plates were dried and stored desiccated in mylar bags.

2F11 MAb Competition Assay Protocol:
2F11 MAb:peroxidase conjugate (0.10 ug/mL) diluted in Tris based buffer containing mouse serum was added to samples (25 µL sample+75 µL conjugate) in an uncoated microtiter dilution plate. The sample:conjugate mixture was mixed by repeated pipetting and dispensing and transferred simultaneously to an IRG2 coated microtiter plate. The microtiter plate was incubated 30 minutes at room temperature. Following incubation the microtiter plate was washed five times with PBS-Tween buffer. A peroxidase substrate was added (50 µL/well) and the plates were incubated for 10 minutes at room temperature. Peroxidase product (activity) was measured with a spectrophotometer (650 nm).

1C9 MAb Competition Assay
IRG2:BSA Plate Coating Protocol
IRG2 polypeptide conjugated to Bovine Serum Albumin (BSA) was coated on microtiter plate (100 µl/well) wells (0.094 µg/mL in 0.05M Sodium Carbonate pH 9.6). Following overnight incubation at room temperature, the plates were washed three times with PBS-Tween buffer. Protein binding sites on the micotiter plate wells were then blocked/overcoated with 2% Tween-20/2.5% Sucrose (300 µL/well). The plates were dried and stored desiccated in mylar bags.

1C9 MAb Competition Assay Protocol:
1C9 MAb:peroxidase conjugate (0.25 µg/mL) diluted in Tris based buffer containing mouse serum was added to samples (50 µL sample+50 µL conjugate) in an uncoated microtiter dilution plate. The sample:conjugate mixture was mixed by repeated pipetting and dispensing and transferred simultaneously to an IGR2:BSA coated microtiter plate. The microtiter plate was incubated 30 minutes at room temperature. Following incubation the microtiter plate was washed five times with PBS-Tween buffer. A peroxidase substrate was added (50 µL/well) and the plates were incubated for 10 minutes at room temperature. Peroxidase product (activity) was measured with a spectrophotometer (650 nm).

Positive and negative results for 2F11 and 1C9 Competition assays were determined using a cutoff set at 40% of the Negative Control OD value; Positive<40% NC OD>Negative.

The 2F11 or 1C9 conjugates prepared as in Example 2 were combined with the samples as described above and added to the coated microtiter wells.

TABLE 2

| N = 124 samples | Aligned Assay | IRG2 Indirect | 2F11 Mab Competition | 1C9 Mab Competition |
|---|---|---|---|---|
| Positive (+) | 80 | 80 | 80 | 81 |
| Negative (−) | 44 | 43 | 44 | 43 |
| Equivocal (+/−) | 0 | 1 | 0 | 0 |

As shown in Table 2, there were two discrepant results: (1) a single sample that tested equivocal in the IRG2 indirect assay tested negative in the Aligned Assay and in the 2F11 and 1C9 competition assays and, (2) a second sample that tested negative in all assays with the exception of the 1C9 competition assay where it was positive.

Figure 2A:
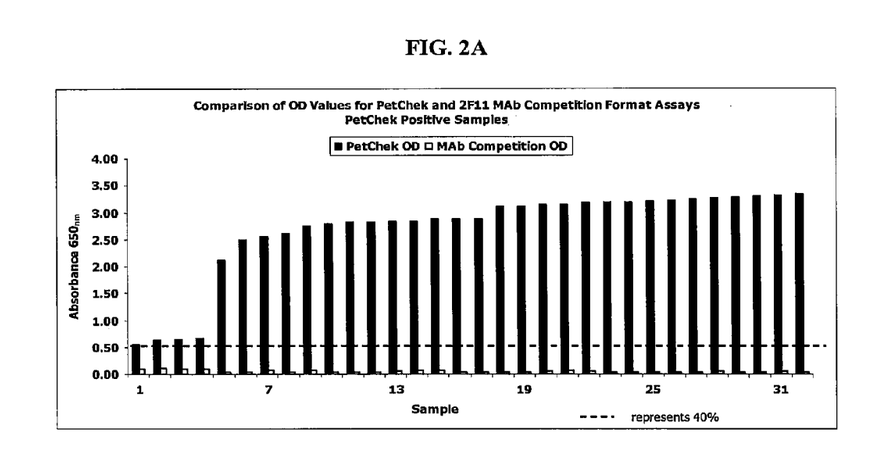
FIG. 2A shows a comparison of assays using the Aligned Assay and the method of the invention (using 2F11 Mabs) on samples confirmed positive for FIV.
Figure 2B:
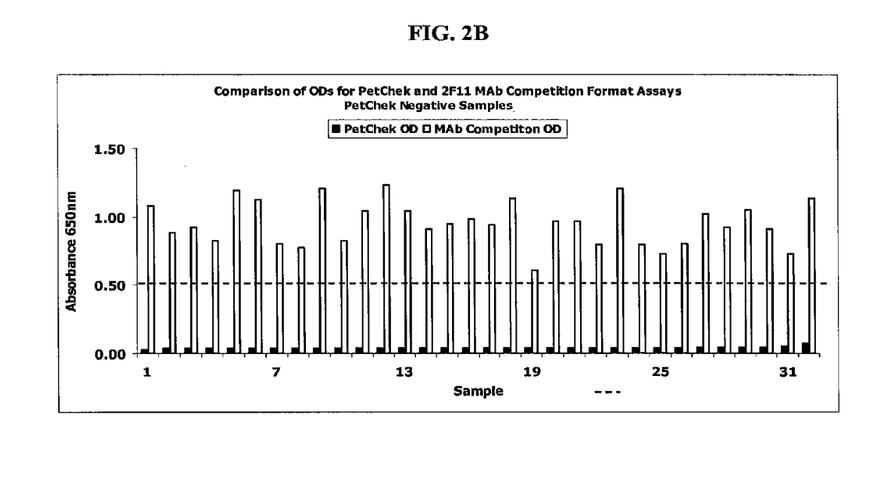
FIG. 2B shows a comparison of assays using the Aligned Assay and the method of the invention (using 2F11 Mabs) on samples confirmed negative for FIV.
Figure 3A:
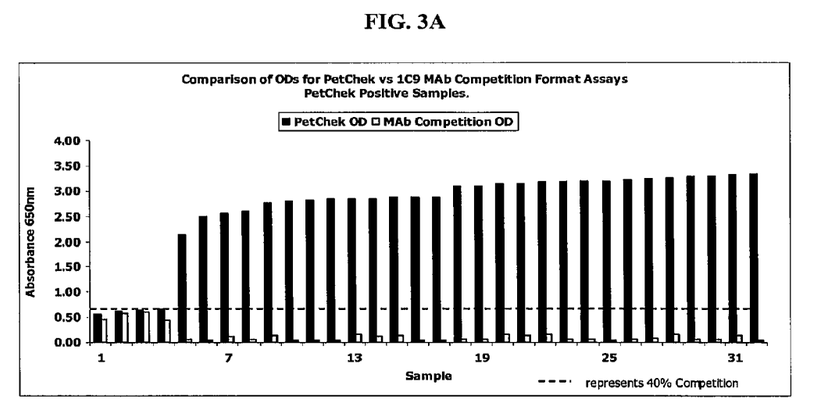
FIG. 3A is the same as FIG. 2A except Mab 1C9 is used.
Figure 3B:
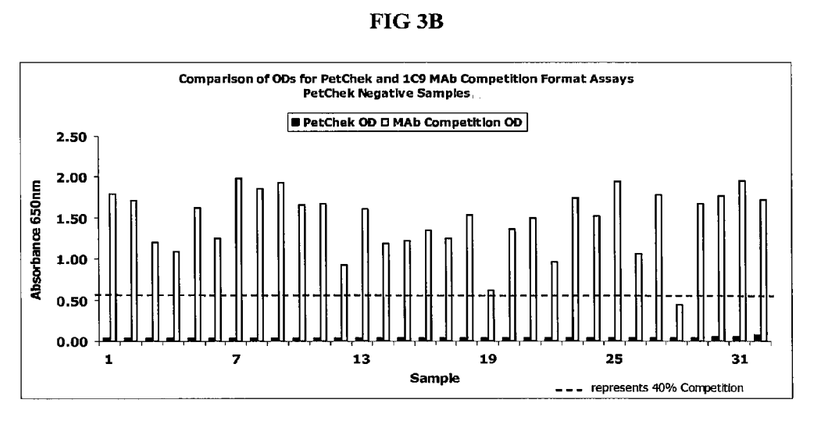
FIG. 3B is the same as FIG. 2B except Mab 1C9 is used.

FIGS. 2A and 2B show a comparison of the optical densities from Aligned Assays and the optical densities of the competitive assay using the 2F11 monoclonal antibody using 32 positive (FIG. 2A) and 32 negative (FIG. 2B) samples. FIGS. 3A and 3B show a comparison of the optical densities from Aligned Assays and the optical densities of the competitive assay using the 1C9 monoclonal antibody using 32 positive (FIG. 3A) and 32 negative (FIG. 3B) samples. As shown in FIG. 2A and FIG. 3A, the 32 samples testing positive in the Aligned Assay provided low OD readings in the competition assays of the invention. In FIG. 2B and FIG. 3B, the 32 samples testing negative in the Aligned Assay provided high OD readings from the competition assays of the invention. The dashed line in the figures represents the cutoff for the competition assay; samples that show competition less than 40% are positive for antibody induced by natural infection or have been vaccinated within the previous five to eight weeks. Samples that show competition greater than 40% are negative for antibody induced by natural infection.

Example 4

Vaccine Temporal Results by 2F11 and 1C9 Competition Assays on Microtiter ELISA

Microplate ELISA analysis was performed on serum samples collected from two cats (IDs 1026 and 1623) vaccinated with one course of the FEL-O-VAX®FIV vaccine (first time vaccinates) and from two cats (IDs B2 and D2) that received one full course of the FEL-O-VAX® vaccine and were subsequently boosted (single inoculation) approximately one year after receiving the initial course of vaccination (re-vaccinates).

The microplate ELISA analysis was performed on sera from the four vaccinates collected at time intervals of one to four weeks starting at week one post vaccination and continuing until week 37 for the first time vaccinates and week 24 post vaccine boost for the re-vaccinates. In the monoclonal antibody competition assays, microtiter plates containing the IRG2 polypeptide bound to the wells were prepared as described above using the 2F11 and 1C9 IRG2:BSA plate coating protocols. Conjugate concentrations were 0.05 µg/mL and 0.25 µg/mL for the 2F11 and 1C9 conjugates, respectively. The assays were carried using the 2F11 and 1C9 MAb competition assay protocols described above.

Figure 4A:
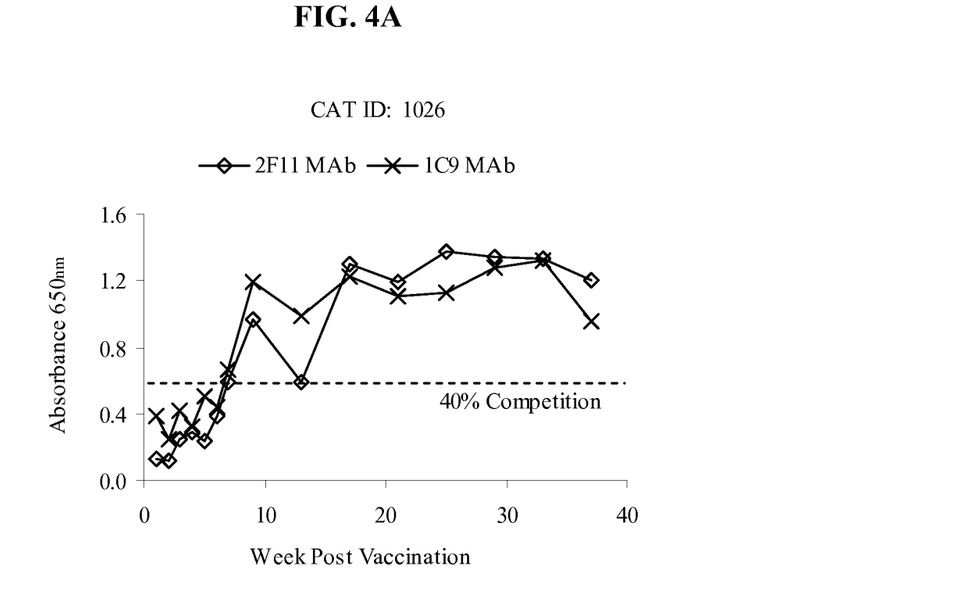
FIGS. 4A and 4B show the results of an assay using one embodiment of the method of the invention in the detection of FIV antibodies in samples taken at various time intervals following vaccination with an FIV vaccine.
Figure 4B:
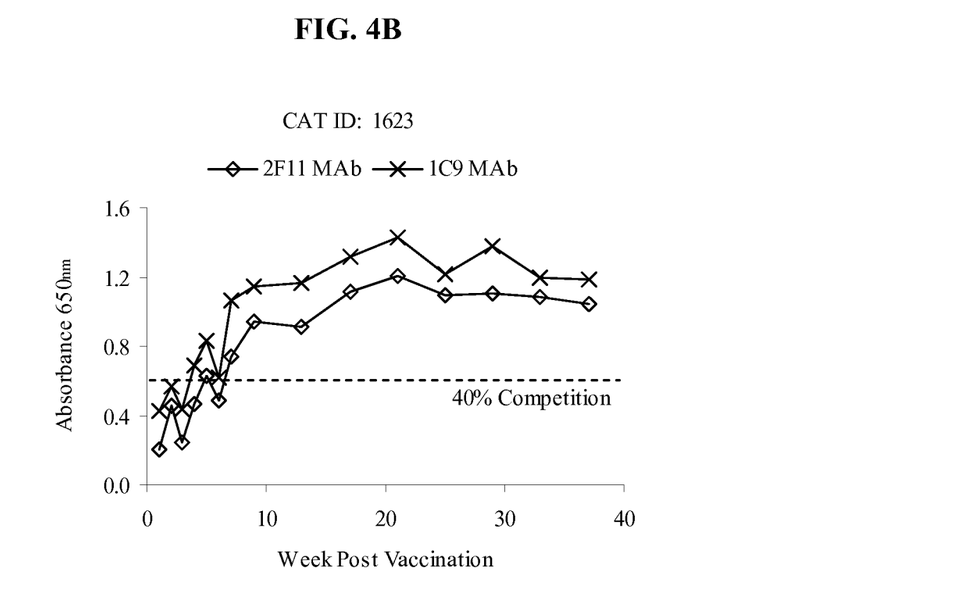
Figure 5A:
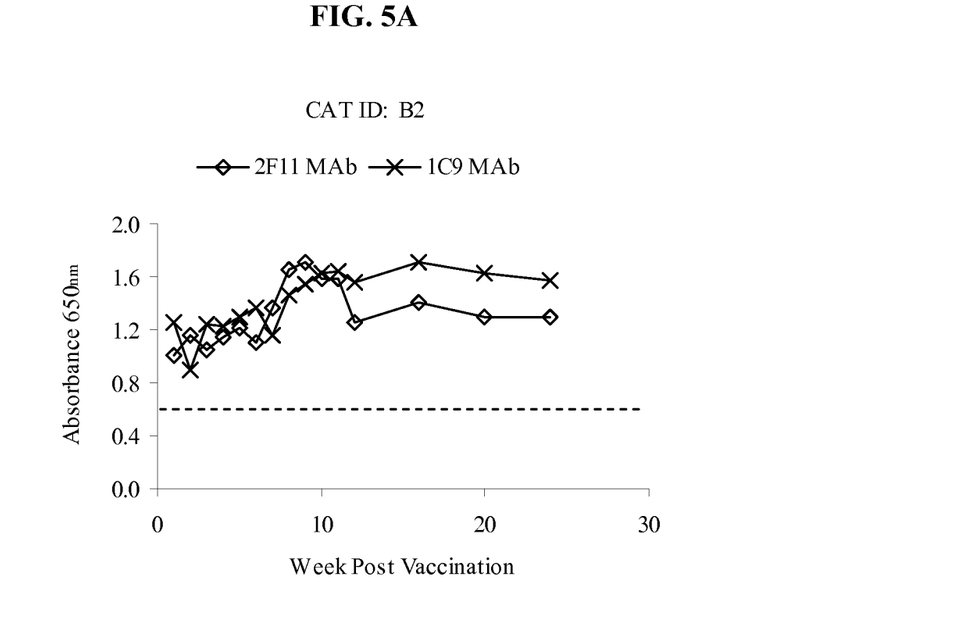
FIGS. 5A and 5B show the results of an assay using one embodiment of the method of the invention in the detection of FIV antibodies in samples taken at various time intervals following vaccination with an FIV vaccine.
Figure 5B:
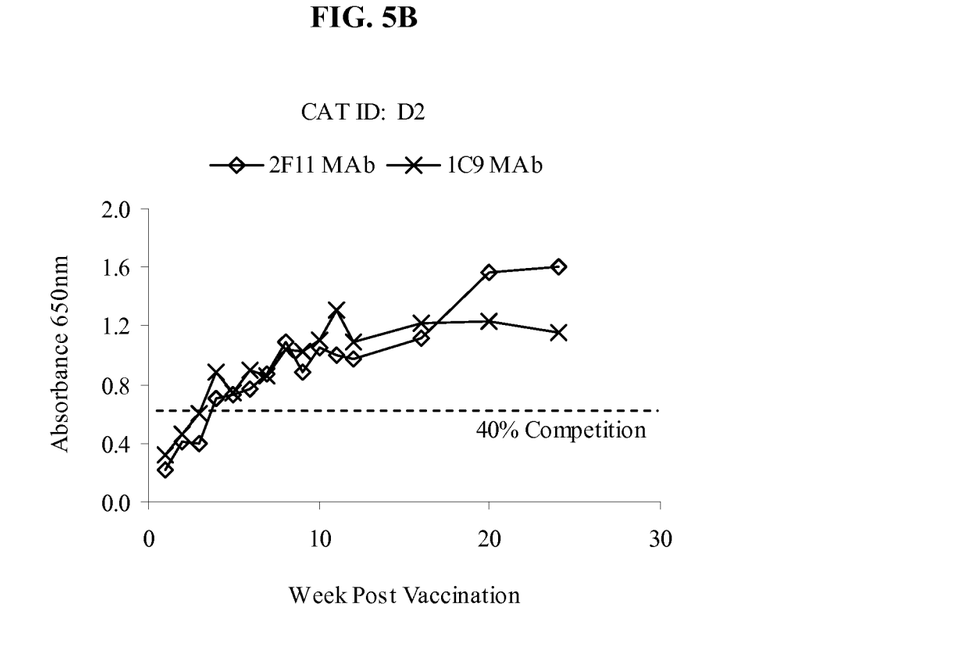

Assay results are shown in FIGS. 4A (cat 1026), 4B (cat 1623), 5A (cat B2) and 5B (cat D2). Samples from the newly vaccinated cats (1026 and 1623) contained antibodies only between 1 and 7 weeks following vaccination. Samples form the re-vaccinated cat D2 contained antibodies only at 1 and 2 weeks post vaccination and samples from re-vaccinated cat B2 did not contain antibodies at any time point. At all time points greater than week 7 post vaccination, samples from both the newly vaccinated and the re-vaccinated felids did not contain detectable antibodies that recognize the IRG2 polypeptide. The 40% competition line is the cutoff for the competition assay; samples that show competition less than 40% are positive for antibody induced by natural infection or have been vaccinated within the previous five to eight weeks and samples that show competition greater than 40% are negative for antibody induced by natural infection.

Example 5

Epitope Mapping of IRG2 Polypeptide

The polypeptides shown in FIG. 1A were synthesized with an N-terminal biotin by conventional methods. The peptides were then coated directly onto a 96 well micro-titre plate as described above for the IRG2 polypeptide. A Streptavidin-HRP conjugate was used to probe the plate, demonstrating the polypeptides were bound thereto. A monoclonal antibody that does not bind IRG2 had been conjugated to HRP and used as a negative control (in this case, BVD MAB 15.C.5, deposited Sep. 16, 1999 by Cornell Research Foundation, Inc., ATCC designation PTA-716). The amount of binding of the 2F11 and 1C9 monoclonal antibodies to the various peptides was determined as described above.

FIG. 1A shows a picture of the microtiter plate and the signal associated with the binding HRP-conjugated monoclonal antibodies to the plate. FIG. 1B shows the relative amount of binding of the monoclonal antibodies to each peptide. From this data, the following epitopes for the 1C9 and 2F11 antibodies were determined (underlined):

```
                                              (SEQ ID NO: 1)
            mAB 1C9  ELGCNQNQFFCK (SEQ ID NO: 1)
            mAB 2F11 ELGCNQNQFFCK
```

Although various specific embodiments of the present invention have been described herein, it is to be understood that the invention is not limited to those precise embodiments and that various changes or modifications can be affected therein by one skilled in the art without departing from the scope and spirit of the invention. While the examples shown herein can differentiate infected and vaccinated cats after five to eight weeks post vaccination, some cats receiving the FEL-O-VAX® vaccine can remain positive for up to 16 to 20 weeks.

What is claimed is:

1. A method for detecting antibodies to Feline Immunodeficiency Virus (FIV) in a biological sample, the method comprising:
   (a) contacting a biological sample from a felid having an unknown vaccination and HIV infection status with the FIV Env polypeptide of SEQ ID NO: 1 (ELGCNQNQFFCK) and a monoclonal antibody that binds to SEQ ID NO: 1,
   (b) detecting whether antibodies in the sample compete with the monoclonal antibody for binding to SEQ ID NO: 1, thereby determining that the sample contains antibodies to FIV, wherein the FIV antibodies in a sample from felids that have been naturally infected will compete with the monoclonal antibody for binding to SEQ ID NO: 1 but antibodies in a sample from felids that have not been infected or felids that have been vaccinated with a whole killed FIV vaccine more than five to eight weeks prior to the sample being obtained will not compete with the monoclonal antibody for binding to SEQ ID NO: 1; and (c) repeating steps (a) and (b) for a second biological sample obtained after about five to eight weeks from the same felid if antibodies in the first biological sample compete with the monoclonal antibody for binding to SEQ ID NO:1 in step (b), wherein the felid is naturally infected if antibodies in the second sample compete with the monoclonal antibody for binding to SEQ ID NO: 1, or the felid has not been infected and has been vaccinated with a whole killed FIV vaccine within about five to eight weeks prior to the first biological sample being obtained if antibodies in the second sample do not compete with the monoclonal antibody for binding to SEQ ID NO: 1.

2. The method of claim 1 wherein the FIV env polypeptide is bound to a solid phase.

3. The method of claim 1 wherein the monoclonal antibody recognizes an epitope contained within the same epitope recognized by a monoclonal antibody produced by one of the hybridoma cell lines having ATCC deposit No. HB10295 (2F11) and ATCC deposit No. PTA-10050 (1C9).

4. The method of claim 1 where the monoclonal antibody is produced by one of the hybridoma cell lines having ATCC deposit No. HB10295 (2F11) and ATCC deposit No. PTA-10050 (1C9).

5. The method of claim 1 wherein competition between an FIV antibody in the sample and the monoclonal antibody is identified when a signal associated with the binding of the monoclonal antibody to SEQ ID NO:1 in the presence of the antibody in the sample is less than about 25-50% of a signal associated with the binding of the monoclonal antibody to SEQ ID NO:1 in the absence of the antibody in the sample.

6. A method for detecting antibodies to Feline Immunodeficiency Virus (FIV) in a biological sample, comprising:
   (a) contacting a biological sample from a felid having an unknown vaccination and HIV infection status and a monoclonal antibody that binds to SEQ ID NO: 1 with a solid phase having SEQ ID NO: 1 immobilized thereon, wherein the monoclonal antibody comprises a label;
   (b) washing the solid phase to remove unbound reagents; and
   (c) detecting the presence of the label at the solid phase, wherein the presence of the label indicates that the felid has not been infected with FIV, and the absence of the label indicates that the felid has been infected with FIV or the felid has been vaccinated with a whole killed FIV vaccine within about the prior five to eight weeks; and
   (d) if the label is absent in the biological sample in step (c), repeating steps (a)-(c) after about five to eight weeks for a second biological sample obtained from the same felid, wherein the presence of the label in the second sample indicates that the felid has been vaccinated with a whole killed FIV about five to eight weeks prior to the sample in step (a) being obtained, and the absence of the label indicates that the felid has been infected with FIV.

7. The method of claim 6 wherein the monoclonal antibody recognizes the same epitope on SEQ ID NO:1 as a monoclonal antibody produced by on one of the hybridoma cell lines having ATCC deposit No. HB10295 (2F11) and PTA-10050 (1C9).

8. The method of claim 6 where the monoclonal antibody is produced by one of the hybridoma cell lines having ATCC deposit No. HB10295 (2F11) and ATCC deposit No. PTA-10050 (1C9).

* * * * *

SEQUENCE LISTING

<160> NUMBER OF SEQ ID NOS: 13

<210> SEQ ID NO 1
<211> LENGTH: 12
<212> TYPE: PRT
<213> ORGANISM: Feline immunodeficiency virus

```
<400> SEQUENCE: 1

Glu Leu Gly Cys Asn Gln Asn Gln Phe Phe Cys Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Ala Leu Gly Cys Asn Gln Asn Gln Phe Phe Cys Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic

<400> SEQUENCE: 3

Ala Ala Gly Cys Asn Gln Asn Gln Phe Phe Cys Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic

<400> SEQUENCE: 4

Glu Ala Ala Cys Asn Gln Asn Gln Phe Phe Cys Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: synthetic

<400> SEQUENCE: 5

Glu Leu Ala Cys Ala Gln Asn Gln Phe Phe Cys Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthtetic

<400> SEQUENCE: 6

Glu Leu Gly Cys Ala Ala Asn Gln Phe Phe Cys Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: synthetic
```

-continued

```
<400> SEQUENCE: 7

Glu Leu Gly Cys Asn Ala Ala Gln Phe Phe Cys Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Glu Leu Gly Cys Asn Gln Ala Ala Phe Phe Cys Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic

<400> SEQUENCE: 9

Glu Leu Gly Cys Asn Gln Asn Ala Ala Phe Cys Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic

<400> SEQUENCE: 10

Glu Leu Gly Cys Asn Gln Asn Gln Ala Ala Cys Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic

<400> SEQUENCE: 11

Glu Leu Gly Cys Asn Gln Asn Gln Phe Ala Cys Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: synthetic

<400> SEQUENCE: 12

Glu Leu Gly Cys Asn Gln Asn Gln Phe Phe Cys Ala
1               5                   10

<210> SEQ ID NO 13
<211> LENGTH: 45
<212> TYPE: PRT
<213> ORGANISM: Artificial Sequence
<220> FEATURE:
<223> OTHER INFORMATION: synthetic
```

```
<400> SEQUENCE: 13

Arg Pro Asp Phe Glu Ser Glu Lys Cys Cys Asn Arg Trp Glu Trp Arg
1               5                   10                  15

Pro Asp Phe Glu Ser Glu Lys Ser Lys Ser Lys Ser Lys Ser Met Gln
                20                  25                  30

Glu Leu Gly Ser Asn Gln Asn Gln Phe Phe Ser Lys Val
            35                  40                  45
```